United States Patent [19]

Hioki et al.

[11] Patent Number: 5,061,796

[45] Date of Patent: Oct. 29, 1991

[54] AZAMETHINE COMPOUNDS

[75] Inventors: Takeshi Hioki, Osaka; Kiyoteru Kojima, Kobe; Jun Tomioka, Ibaraki, all of Japan

[73] Assignee: Sumitomo Chemical Company, Limited, Osaka, Japan

[21] Appl. No.: 383,081

[22] Filed: Jul. 21, 1989

Related U.S. Application Data

[62] Division of Ser. No. 179,251, Apr. 8, 1988, Pat. No. 5,028,708.

[30] Foreign Application Priority Data

Apr. 14, 1987 [JP] Japan .................................. 62-91146
Dec. 22, 1987 [JP] Japan .................................. 62-325998
Jan. 21, 1988 [JP] Japan .................................. 63-11078

[51] Int. Cl.$^5$ ...................... G11B 7/24; C07C 121/84; C07D 417/12; C07D 409/12
[52] U.S. Cl. ...................................... 544/163; 430/72; 558/260; 558/262; 558/269; 558/271; 558/411; 558/414; 558/416; 558/417; 558/419; 558/426
[58] Field of Search ................ 544/163; 558/260, 262, 558/269, 271, 272, 411, 414, 415, 416, 417, 419, 426; 430/72

[56] References Cited

U.S. PATENT DOCUMENTS

| | | | |
|---|---|---|---|
| 3,162,641 | 12/1964 | Acker et al. | 546/167 |
| 4,146,627 | 3/1979 | Wehinger et al. | 546/167 |
| 4,281,115 | 7/1981 | Baumann | 430/72 |
| 4,460,665 | 7/1984 | Kunikane et al. | 548/199 |

FOREIGN PATENT DOCUMENTS 3533545 5/1987 Fed. Rep. of Germany ...... 546/171

OTHER PUBLICATIONS

Chetking et al., Zhurnal Struch. Khim 26 (5) 1985, pp. 115–119.
Chemical Abstracts, vol. 100, No. 24, Jun. 11, 1984, p. 588.
Chemical Abstracts, vol. 104, No. 8, Feb. 24, 1986, No. 59741m.
Bello et al., "Near-Infrared Absorbing Methine Dyes", Journ. Chem. Soc., Perkin Transactions II, No. 6, pp. 815–818, Jun. 1987.

*Primary Examiner*—Mukund J. Shah
*Assistant Examiner*—E. C. Ward
*Attorney, Agent, or Firm*—Stevens, Davis, Miller & Mosher

[57] ABSTRACT

This invention provides azamethine compounds represented by the formula (I):

(wherein X represents (Abstract continued on next page.)

-continued

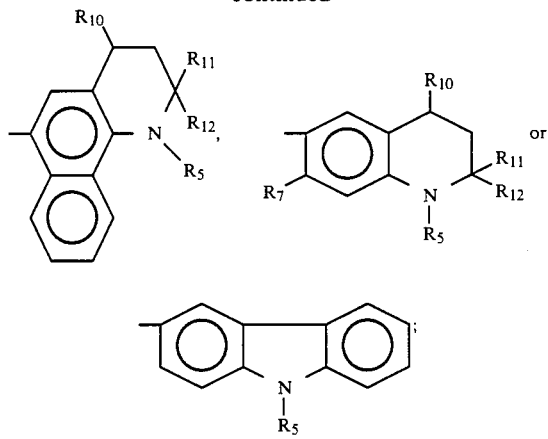

Y represents C=O, C=C(CN)$_2$ or SO$_2$; R$_1$ to R$_4$ represent independently a hydrogen atom, an alkyl group which may be substituted, an alkoxyl group which may be substituted, a halogen atom, a nitro group, a cyano group, a hydroxyl group, an amino group which may be substituted,

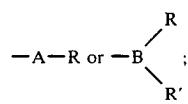

R$_5$ and R$_6$ represent independently a hydrogen atom, an alkyl group which may be substituted, an aryl group which may be substituted or a cyclohexyl group; R$_5$ and R$_6$ may be combined to form a ring or may form a ring with a hetero atom; R$_7$ and R$_8$ represent independently a hydrogen atom, an alkyl group which may be substituted, an alkoxy group which may be substituted, a hydroxyl group, a halogen atom, a nitro group, a cyano group,

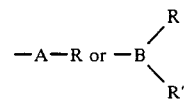

wherein -A represents

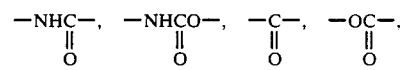

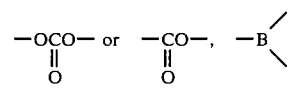

represents

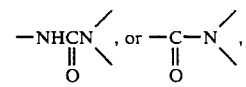

and R and R' represent independently a hydrogen atom, an alkyl group which may be substituted, an aryl group which may be substituted, a heterocyclic group or a cyclohexyl group; R$_9$ represents a hydrogen atom, an alkyl group which may be substituted, or an aryl or heteroaryl group which may be substituted; and R$_{10}$ to R$_{12}$ represent independently a hydrogen atom or an alkyl group), a process for producing such compounds, and a medium for recording optical information using these compounds.

6 Claims, 10 Drawing Sheets

AZAMETHINE COMPOUNDS

This is a division of application Ser. No. 07/179,251 filed Apr. 8, 1988 now U.S. Pat. No. 5,028,108.

This invention relates to azamethine compounds, a process for preparing the same, and a medium for recording optical information using such compounds.

The compounds of this invention find their use not only for a medium for recording optical information as mentioned above but also for various other electrochemical devices including fine-color separation filters for color image pickup devices and color displays, sharp cut filters for infrared ray sensors, photoconductive organic compositions, dye lasers, etc.

The optical information recording media, for which the use of the compounds of this invention is especially envisaged, have as a prominent feature that they suffer from no problems due to wear because of the structural peculiarity that the medium itself is not contacted with the writing and reading head. In view of such and other advantages, many studies have been made for the development of various types of optical information media.

Among these optical information recording media, the so-called heat mode optical information recording medium is attracting attention and ardent studies are being made on this type of optical information recording medium because this recording medium does not necessitate the developing in a dark place. This heat mode optical recording medium is a type of optical information recording medium which utilizes recording light as a heat source. As a typical example of such a heat mode optical recording medium, there is known a pit-forming type in which the medium is partly melted and removed by a recording light, such as laser, to form small holes called pits for recording information. These pits are detected by the reading light for the read out of the recorded information.

Thus, the optical information recording media are required to be able to absorb the energy of a laser light with high efficiency, for which it is necessary that said media have high absorptivity of the laser light of specific wavelengths used for recording. They also must have a high reflectance for laser light of the specific wavelengths used for the regeneration of the information to allow the correct regeneration of the information.

In most of such pit-forming type recording media, especially those using a semiconductor laser as the light source with which a dimensional reduction of the apparatus was possible, a material mainly composed of Te has been used for the recording layer.

Recently, however, because of the problem of environmental pollution involved in the use of such Te-based material and also in view of the necessity for higher sensitivity and lower production cost, many proposals and reports have been made on recording media using a recording layer made of an organic material mainly composed of an organic dye instead of a Te-based material.

As the dyes usable for such organic material, there have been proposed cyanine dyes (see, for example, Japanese Patent Application Kokai (Laid-Open) No. 114989/83), metal complex dyes (see, for example, Japanese Patent Application Kokai (Laid-Open) No. 16888/83), etc.

These compounds, however, are unstable for storage in the air and for light in a thin film. Various methods for the stabilization thereof have been proposed (as for instance in Japanese Patent Application Kokai (Laid-Open) No. 55794/84), and efforts for further improvement are still being made.

The present invention is intended to provide a medium for recording optical information which has high absorptivity and reflectivity of semiconductor laser light and is also stable in light and heat.

As a result of assiduous studies for improving said defects of the conventional materials for optical recording media, the present inventors have found that the azamethine compounds represented by the following general formula (I) are stable and especially useful as a recording material, and the present invention was achieved on the basis of such finding.

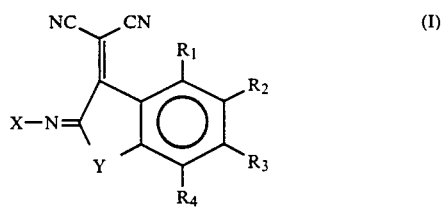

(wherein X represents

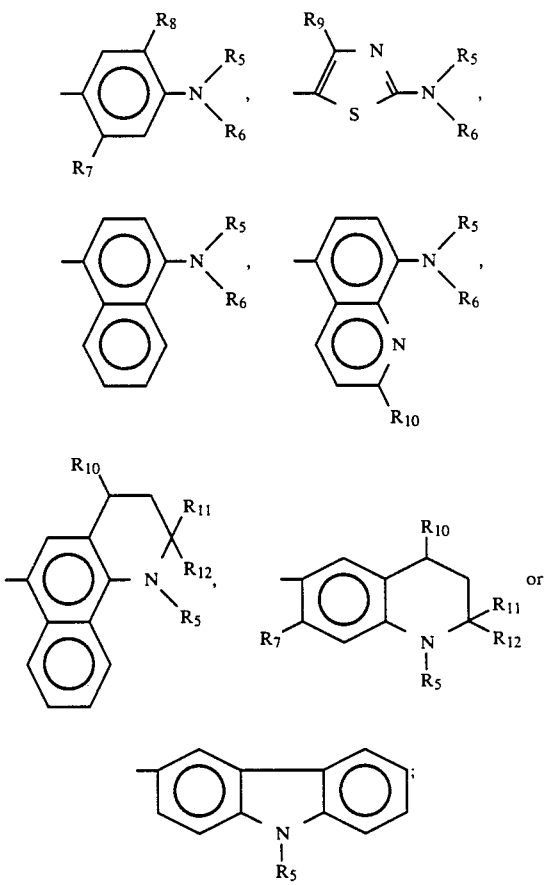

Y represents $C=O$, $C=C(CN)_2$ or $SO_2$; $R_1$ to $R_4$ represent independently a hydrogen atom, an alkyl group which may be substituted, an alkoxyl group which may be substituted, a halogen atom, a nitro group, a cyano group, a hydroxyl group, an amino group which may be substituted,

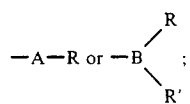

$R_5$ and $R_6$ represent independently a hydrogen atom, an alkyl group which may be substituted, an aryl group which may be substituted or a cyclohexyl group; $R_5$ and $R_6$ may be combined to form a ring or may form a ring with a hetero atom; $R_7$ and $R_8$ represent independently a hydrogen atom, an alkyl group which may be substituted, an alkoxyl group which may be substituted, a hydroxyl group, a halogen atom, a nitro group, a cyano group,

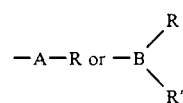

wherein —A represents

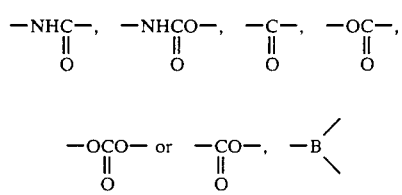

represents

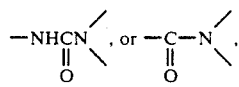

and R and R' represent independently a hydrogen atom, an alkyl group which may be substituted, an aryl group which may be substituted, a heterocyclic residue or a cyclohexyl group; $R_9$ represents a hydrogen atom, an alkyl group which may be substituted, or an aryl or heteroaryl group which may be substituted; and $R_{10}$ to $R_{12}$ represent independently a hydrogen atom or an alkyl group, with the proviso that X represents

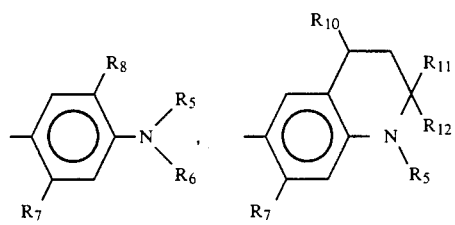

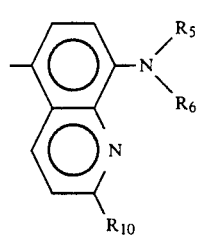

(wherein $R_5$ and $R_6$ represent independently a hydrogen atom, an alkyl group which may be substituted, an aryl group which may be substituted or a cyclohexyl group; $R_5$ and $R_6$ may be combined to form a ring or may form a ring with a hetero atom; $R_7$ represents an alkyl group which may be substituted, an alkoxyl group which may be substituted, a hydroxyl group, a halogen atom or

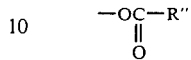

wherein R" represents an alkyl group which may be substituted; $R_8$ represents a hydrogen atom, an alkyl group which may be substituted, an alkoxyl group which may be substituted or a halogen atom; and $R_{10}$ to $R_{12}$ represent independently a hydrogen atom or an alkyl group), when Y represents $C=C(CN)_2$.).

More specifically, the present invention found that the azamethine compounds represented by the following formula (II) are very stable and more useful as a recording material;

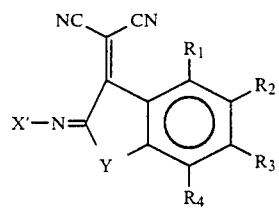

wherein Y represents $C=O$, $C=C(CN)_2$ or $SO_2$; $R_1$ to $R_4$ are as defined above; and X' represents

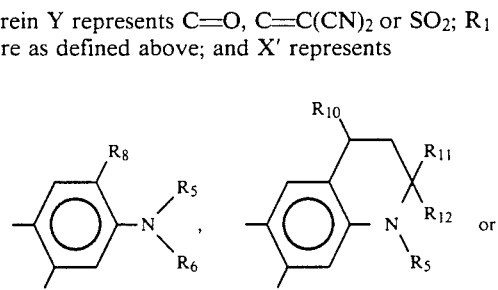

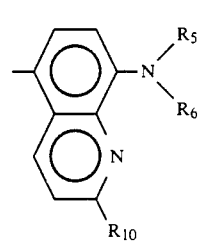

(wherein $R_5$ and $R_6$ represent independently a hydrogen atom, an alkyl group which may be substituted, an aryl group which may be substituted or a cyclohexyl group; $R_5$ and $R_6$ may be combined to form a ring or may form a ring with a hetero atom; $R_7$ represents an alkyl group which may be substituted, an alkoxyl group which may be substituted, a hydroxyl group, a halogen atom or

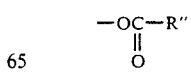

wherein R" represents an alkyl group which may be substituted; $R_8$ represents a hydrogen atom, an alkyl group which may be substituted, an alkoxyl group which may be substituted or a halogen atom; and $R_{10}$ to $R_{12}$ represent independently a hydrogen atom or an alkyl group).

Among the compounds represented by the above-shown formula (II), the following are especially preferred:
the azamethine compounds of the formula (II) wherein Y is C=O or C=C(CN)$_2$;
the azamethine compound of formula (II) wherein $R_7$ is an alkyl group which may be substituted or an alkoxyl group which may be substituted;
the azamethine compounds of formula (II) wherein Y is C=O and $R_7$ is an alkyl group which may be substituted; and the azamethine compounds of formula (II) wherein Y is C=C(CN)$_2$ and $R_7$ is an alkoxyl group which may be substituted.

The compounds represented by the formula (I) according to this invention can be produced by condensing the compounds represented by formula (III):

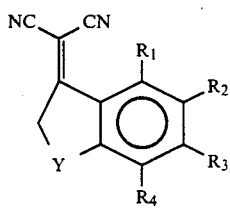   (III)

(wherein Y represents C=O, C=C(CN)$_2$ or SO$_2$; $R_1$ to $R_4$ represent independently a hydrogen atom, an alkyl group which may be substituted, an alkoxyl group which may be substituted, a halogen atom, a nitro group, a cyano group, a hydroxyl group, an amino group which may be substituted,

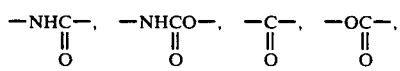

wherein —A— represents

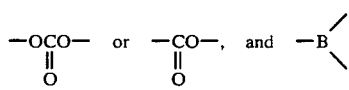

represents

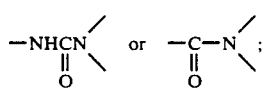

and R and R' represent independently a hydrogen atom, an alkyl group which may be substituted, an aryl group which may be substituted, a heterocyclic residue or a cyclohexyl group) and the compounds represented by formula (IV):

X—N=O   (IV)

(wherein X represents

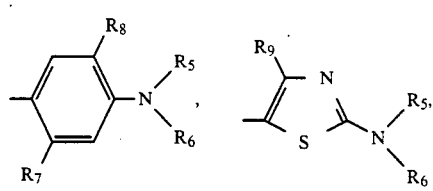

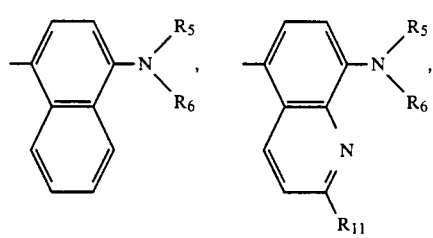

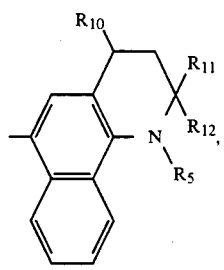

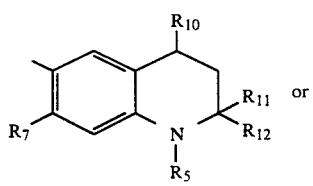

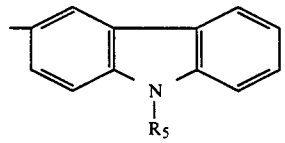

wherein $R_5$ and $R_6$ represent independently a hydrogen atom, an alkyl group which may be substituted, an aryl group which may be substituted or a cyclohexyl group; $R_5$ and $R_6$ may be combined to form a ring or may form a ring with a hetero atom; $R_7$ and $R_8$ represent independently a hydrogen atom, an alkyl group which may be substituted, an alkoxyl group which may be substituted, a hydroxyl group, a halogen atom, a nitro group, a cyano group,

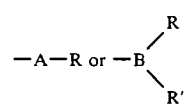

wherein —A— represents

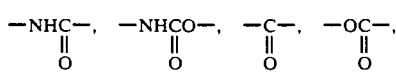

-continued

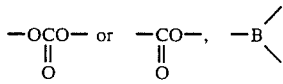

represents

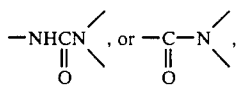

and R and R' represent independently a hydrogen atom, an alkyl group which may be substituted, an aryl group which may be substituted, a heterocyclic residue or a cyclohexyl group; $R_9$ represents a hydrogen atom, an alkyl group which may be substituted, or an aryl or heteroaryl group which may be substituted; and $R_{10}$ to $R_{12}$ represent independently a hydrogen atom or an alkyl group, with the proviso that X represents

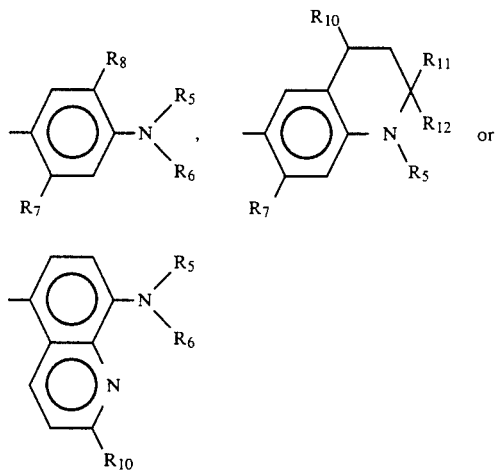

(wherein $R_5$ and $R_6$ represent independently a hydrogen atom, an alkyl group which may be substituted, an aryl group which bay be substituted or a cyclohexyl group; $R_5$ and $R_6$ may be combined to form a ring or may form a ring with a hetero atom; $R_7$ represents an alkyl group which may be substituted, an alkoxyl group which may be substituted, a hydroxyl group, a halogen atom or

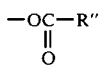

wherein R" represents an alkyl group which may be substituted; $R_8$ represents a hydrogen atom, an alkyl group which may be substituted, an alkoxyl group which may be substituted or a halogen atom; and $R_{10}$ to $R_{12}$ represent independently a hydrogen atom or an alkyl group), when Y represents $C=C(CN)_2$.).

Said condensation reaction is carried out using an inert organic solvent such as methanol, ethanol, n-propanol, acetic acid, toluene, chlorobenzene, chloroform, dimethylformamide, N-methylpyrrolidone, dimethyl sulfoxide, sulforan, acetonitrile, acetic anhydride and the like.

A compound of formula (III) and a compound of formula (IV) are mixed in an inert organic solvent such as mentioned above, a catalyst such as preferably piperidine, pyridine, triethylamine or an organic base such as a mixture of piperidine and glacial acetic acid is further added and the mixture reacted at 0°~100° C., preferably 20°~80° C. for 0.5~10 hours, preferably 1~5 hours. The reaction mixture is cooled and filtered to give the crude cakes of a compound of this invention represented by the formula (I). Such crude cakes may be purified by recrystallization from a proper solvent or by other means.

The structures of the optical information recording media using an azamethine compound of this invention and the transmittance and reflectance spectra of such recording media measured by irradiating the media via the substrate are shown in the accompanying drawings in which.

Figure 1:
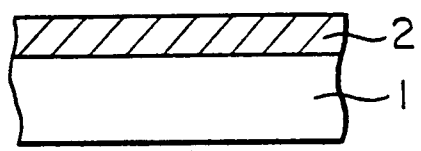
FIGS. 1 to 4 are sectional views showing the structures of the optical information recording media according to this invention. In the drawings, reference numeral 1 indicates a substrate, 2 a recording layer, 3 an underlayer, and 4 a protective layer.
Figure 2:
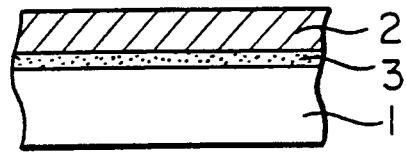
Figure 3:
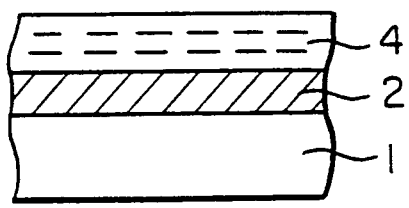
Figure 4:
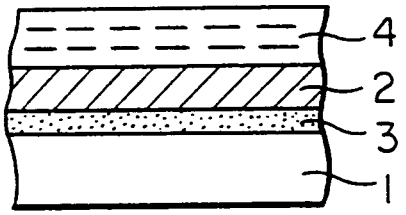

The optical information recording media using an azamethine compound obtained according to the process of this invention have the basic structure shown in FIG. 1, and where necessary an underlayer and/or a protective layer may be further provided as shown in FIGS. 2 to 4. Two pieces of recording medium having the same structure may be combined so that the recording layers 2 of the respective recording media will be positioned on the inside facing each other to form a so-called air sandwich structure. Also, two pieces of recording medium may be bonded to each other with a protective layer 4 interposed therebetween. In these recording media, the recording of information is made by shape changes of the membrane caused by the thermal action of a laser light, and the regeneration of the information is made by detecting the difference between reflected light from the section which had a shape change and that from the section with no shape change.

The formation of the recording layer may be accomplished by ordinary means such as vacuum deposition or solution coating. The recording layer may be formed by using one dye of this invention or a mixture of two or more of the dyes of this invention. Also, the dye(s) of this invention may be used in combination with other dye(s), in the form of mixture, laminate, etc. The dyes of this invention may be used by mixing or dispersing them in a high-molecular material such as silicone, polyamide resin, vinyl resin, natural polymers, etc., or other materials such as a silicone coupling agent. Also, they may be used with a stabilizer, dispersing agent, antistatic agent and the like.

The thickness of the recording layer in the recording media of this invention is in the range of 50 to 5,000 ∪, preferably 100 to 2,000 ∪.

The substrate material used in this invention is one which is transparent to laser beams. Examples of such material are glass, quartz, and various types of plastics such as polycarbonate resin, vinyl chloride resin, polymethyl methacrylate resin (PMMA), polyester resin, polyethylene resin, polypropylene resin, polyamide resin, polystyrene resin, epoxy resin, and other mono- and copolymers.

Underlayer 3 is provided for the purposes of protecting the substrate from the solvent, improving the adhesiveness, forming a pregroove, etc. Said high-molecular materials, silane coupling agents, inorganic compounds ($SiO_2$, $MgF_2$, ZnO, etc.), ultraviolet-cured resins, thermosetting resins and the like can be used as the underlayer material.

The thickness of such underlayer is in the range of 0.1 to 30 μm, preferably 0.2 to 10 μm.

Protective layer 4 is provided for the purposes of protecting the substrate from dirt and dust and improving the chemical stability of the recording layer.

The thickness of such protective layer should be not less than 0.1 μm, preferably not less than 50 μm.

The films of the novel azamethine compounds according to this invention show an absorption maximum in the wavelength region of 600 to 850 nm, have a high reflectance in the region of 600 to 900 nm and are also very stable, so that the films of the compounds of this invention find a wide scope of uses and are particularly useful as media for recording optical information.

The present invention will hereinafter be described in more detail with reference to the Examples thereof, but it is to be understood that these Examples are merely intended to be illustrative and not to be construed as limiting the scope of the invention.

In the Examples shown below, the measurement of the spectrum was made by irradiating the medium via the substrate using a spectrophotometer Model UV-365 mfd. by Shimazu Seisakusho Co., Ltd. The measurement of the thickness was made using a film thickness gauge Talystep mfd. by Taylor & Hobson Inc.

EXAMPLE 1

0.50 g of the compound of formula (1):

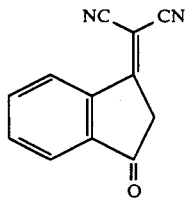
(1)

and 0.94 g of the compound of formula (2):

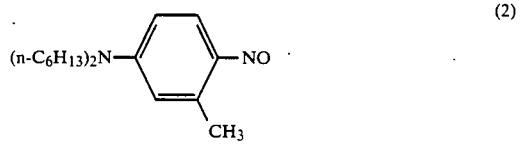
(2)

were mixed in 10 ml methanol. To the solution was added 0.2 g of piperidine. The solution was stirred at 40° C. for 2 hours and cooled to 5° C. The mixed solution was filtered, washed with ice-cold methanol and dried. The resulting product was recrystallized from chloroform to obtain 0.87 g of purified cakes of the compound of the following formula (3). Yield: 70.3%. Melting point: 228°~230° C. Absorbance in acetone solution: $\lambda max = 701$ nm, $\epsilon = 3.23 \times 10^4$.

NMR in $CDCl_3$: 0.92 ppm (6H), 1.35 ppm (12H), 1.68 ppm (4H), 2.66 ppm (3H), 3.43 ppm (4H), 6.50 ppm (1H), 6.57 ppm (1H), 7.70 ppm (2H), 7.85 ppm (2H), (8.62 ppm (1H).

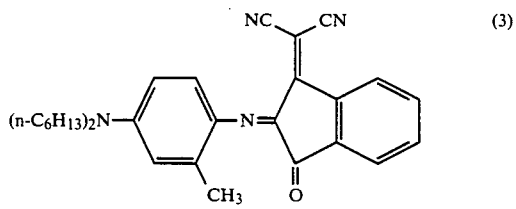
(3)

EXAMPLE 2

1.00 g of the compound of formula (4):

(4)

and 1.69 g of the compound of formula (5):

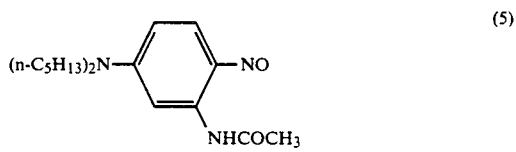
(5)

were mixed in 20 ml of methanol, followed by the addition of 0.5 g of piperidine. The mixed solution was stirred at 50° C. for 2 hours and then cooled to 5° C. The mixed solution was filtered, washed with ice-cold methanol and dried. The resulting product was recrystallized from chloroform to obtain 1.42 g of purified cakes of the compound of the following formula (6). Yield: 61.0%. Melting point: 164°~164.5° C. Absorbance in acetone solution: $\lambda max = 674$ nm; $\epsilon = 6.14 \times 10^4$.

NMR in $CDCl_3$: 0.94 ppm (6H), 1.37 ppm (8H), 1.72 ppm (4H), 2.32 ppm (3H), 3.50 ppm (4H), 6.58 ppm (1H), 7.82 ppm (1H), 7.93 ppm (2H), 8.12 ppm (1H), 8.25 ppm (1H), 8.87 ppm (1H), 9.70 ppm (1H).

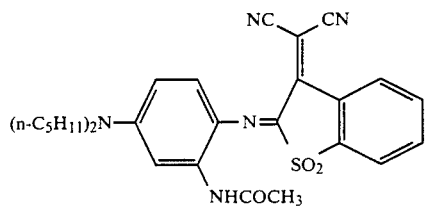 (6)

The compounds shown in Table 1 below were produced in the same way as Example 1 or Example 2.

TABLE 1

General formula:

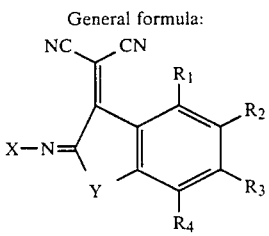

| No. | R₁ | R₂ | R₃ | R₄ | Y | X | Absorption maximum wavelength in acetone (nm) |
|---|---|---|---|---|---|---|---|
| 3 | H | H | H | H | $\overset{\text{C}}{\underset{\text{O}}{\parallel}}$ | (C₂H₅)₂N—⟨phenyl⟩— with CH₃ | 700 |
| 4 | H | H | H | H | $\overset{\text{C}}{\underset{\text{O}}{\parallel}}$ | (⟨phenyl⟩—CH₂)₂N—⟨phenyl⟩— with CH₃ | 702 |
| 5 | H | H | H | H | $\overset{\text{C}}{\underset{\text{O}}{\parallel}}$ | n-C₅H₁₁, NCC₂H₄—N—⟨phenyl⟩— with NHCOCH₃ | 685 |
| 6 | H | H | H | H | $\overset{\text{C}}{\underset{\text{O}}{\parallel}}$ | ⟨phenyl⟩—HN—⟨phenyl⟩— with C₃H₇(i) | 700 |
| 7 | H | H | H | H | $\overset{\text{C}}{\underset{\text{O}}{\parallel}}$ | CH₃COOC₂H₄, n-C₅H₁₁—N—⟨phenyl⟩— with CH₃ | 709 |
| 8 | H | H | H | H | $\overset{\text{C}}{\underset{\text{O}}{\parallel}}$ | CH₃O(CH₂)₂OC₂H₄, C₂H₅—N—⟨phenyl⟩— with C₂H₅ | 708 |

TABLE 1-continued

General formula:

$$\begin{array}{c} NC \diagdown \diagup CN \\ \parallel \\ X-N \diagdown \diagup \\ Y \end{array} \begin{array}{c} R_1 \\ R_2 \\ R_3 \\ R_4 \end{array}$$

| No. | R$_1$ | R$_2$ | R$_3$ | R$_4$ | Y | X | Absorption maximum wavelength in acetone (nm) |
|-----|-------|-------|-------|-------|---|---|------|
| 9 | H | H | H | H | $\overset{\text{C}}{\underset{\text{O}}{\parallel}}$ | (HOC$_2$H$_4$)$_2$N–⟨phenyl with CH$_3$⟩ | 701 |
| 10 | H | H | H | H | $\overset{\text{C}}{\underset{\text{O}}{\parallel}}$ | (C$_2$H$_5$)$_2$N–⟨phenyl with CH$_3$O, CH$_3$⟩ | 720 |
| 11 | H | H | H | H | $\overset{\text{C}}{\underset{\text{O}}{\parallel}}$ | (n-C$_5$H$_{11}$)$_2$N–⟨phenyl with CH$_3$O, CH$_3$⟩ | 721 |
| 12 | H | H | H | H | $\overset{\text{C}}{\underset{\text{O}}{\parallel}}$ | (C$_2$H$_5$)$_2$N–⟨phenyl with CH$_2$–phenyl⟩ | 702 |
| 13 | H | H | H | H | $\overset{\text{C}}{\underset{\text{O}}{\parallel}}$ | (n-C$_4$H$_9$)$_2$N–⟨phenyl with OH⟩ | 660 |
| 14 | H | H | H | H | $\overset{\text{C}}{\underset{\text{O}}{\parallel}}$ | cyclohexyl-N(n-C$_4$H$_9$)–⟨phenyl with Cl⟩ | 690 |
| 15 | H | H | H | H | $\overset{\text{C}}{\underset{\text{O}}{\parallel}}$ | morpholino–⟨phenyl with OCH$_3$⟩ | 661 |

TABLE 1-continued

General formula:

$$\text{X-N=}\underset{Y}{\overset{}{\text{C}}}\text{-C(CN)=C(CN)}_2 \text{ with phenyl bearing } R_1, R_2, R_3, R_4$$

| No. | R₁ | R₂ | R₃ | R₄ | Y | X | Absorption maximum wavelength in acetone (nm) |
|---|---|---|---|---|---|---|---|
| 16 | H | H | H | H | C=O | 4-CH₃-C₆H₄-O(CH₂)₂-N(C₂H₅)-C₆H₄-4-CH₃ (via para position) | 691 |
| 17 | H | H | H | H | C=O | 2-[(CH₃)₂C(CH₃)-CH₂-CH(CH₃)-]-4,5-(CH₃)₂-C₆H₂-N(C₂H₅)- (tetrahydroquinoline-type) | 701 |
| 18 | H | H | H | H | C=O | same as 17 with N-C₃H₇(i) | 703 |
| 19 | H | H | H | H | C=O | same as 17 with N-C₄H₉(n) | 702 |
| 20 | H | H | H | H | C=O | same as 17 with N-C₆H₁₃(n) | 700 |
| 21 | H | H | H | H | C=O | same as 17 with N-C₂H₄-C₆H₅ | 701 |

TABLE 1-continued

General formula:

$$\begin{array}{c} NC \quad CN \\ X-N=C \\ \phantom{X-N=}| \\ \phantom{X-N=}Y \end{array} \text{—Ar}(R_1, R_2, R_3, R_4)$$

| No. | $R_1$ | $R_2$ | $R_3$ | $R_4$ | Y | X | Absorption maximum wavelength in acetone (nm) |
|---|---|---|---|---|---|---|---|
| 22 | H | H | H | H | C=O | 2,4-diethyl-substituted phenyl with N(C$_2$H$_5$)(CH$_2$C(CH$_3$)$_2$CH$_3$), CH$_3$ branch | 704 |
| 23 | H | H | H | H | C=O | 2,5-dimethyl-substituted phenyl with N(C$_2$H$_4$OH)(CH$_2$C(CH$_3$)$_2$CH$_3$), CH$_3$ branch | 702 |
| 24 | H | H | H | H | C=O | 4-isopropyl-substituted phenyl with N(C$_2$H$_5$)(CH$_2$C(CH$_3$)$_2$CH$_3$), CH$_3$ branch | 705 |
| 25 | H | H | H | H | C=O | 4-methoxy-substituted phenyl with N(C$_2$H$_5$)(CH$_2$C(CH$_3$)$_2$CH$_3$), CH$_3$ branch | 642 |
| 26 | H | H | H | Cl | C=O | 3-methyl-4-(diethylamino)phenyl | 713 |
| 27 | H | H | H | H | C=O | methyl-substituted phenyl with N(CH$_3$)(CH$_2$C(CH$_3$)$_2$CH$_3$), CH$_3$ branch | 630 |

TABLE 1-continued
General formula:
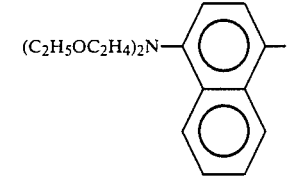
| No. | R₁ | R₂ | R₃ | R₄ | Y | X | Absorption maximum wavelength in acetone (nm) |
|---|---|---|---|---|---|---|---|
| 28 | H | H | H | H | $\underset{O}{\overset{\|}{C}}$ | 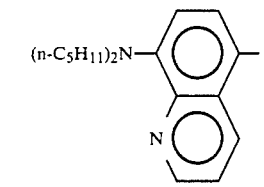 | 701 |
| 29 | H | H | H | H | $\underset{O}{\overset{\|}{C}}$ | 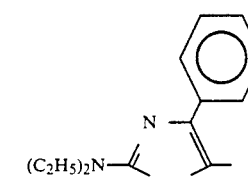 | 670 |
| 30 | H | H | H | H | $\underset{O}{\overset{\|}{C}}$ | 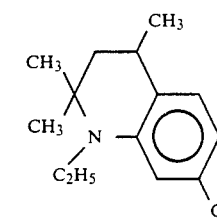 | 731 |
| 31 | H | H | H | Cl | $\underset{O}{\overset{\|}{C}}$ | 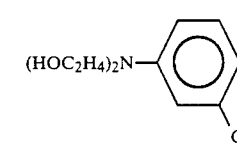 | 713 |
| 32 | H | H | H | Cl | $\underset{O}{\overset{\|}{C}}$ | 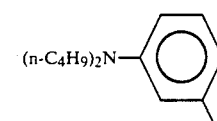 | 710 |
| 33 | H | H | H | Cl | $\underset{O}{\overset{\|}{C}}$ | (n-C₄H₉)₂N—⌬—CH₃ | 714 |

TABLE 1-continued

General formula:

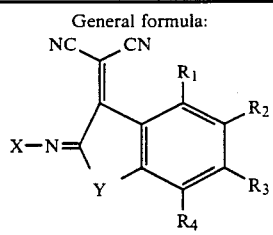

| No. | R₁ | R₂ | R₃ | R₄ | Y | X | Absorption maximum wavelength in acetone (nm) |
|---|---|---|---|---|---|---|---|
| 34 | H | H | H | Cl | $\overset{\text{O}}{\underset{\|}{\text{C}}}$ | 4-(N-n-butyl-N-(2-methyl-4-(3,5-dimethylphenyl))pentyl)amino substituted aryl | 715 |
| 35 | H | H | H | Cl | $\overset{\text{O}}{\underset{\|}{\text{C}}}$ | N-n-hexyl analog | 715 |
| 36 | H | H | H | Cl | $\overset{\text{O}}{\underset{\|}{\text{C}}}$ | N-(2-hydroxyethyl) analog | 712 |
| 37 | H | H | Br | H | $\overset{\text{O}}{\underset{\|}{\text{C}}}$ | 4-(di-n-pentylamino)-2-methoxy-5-(n-propanoylamino)phenyl | 731 |
| 38 | H | H | NO₂ | H | $\overset{\text{O}}{\underset{\|}{\text{C}}}$ | 4-(N-n-hexyl-N-ethyl)amino-2,3-dimethylphenyl | 742 |
| 39 | H | H | NO₂ | H | $\overset{\text{O}}{\underset{\|}{\text{C}}}$ | N-methyl-naphthyl derivative | 746 |

TABLE 1-continued

General formula:

$$\begin{array}{c} NC \quad CN \\ \diagdown \diagup \\ C \\ \parallel \\ X-N=C \quad \text{Ar}(R_1,R_2,R_3,R_4) \\ \quad \quad | \\ \quad \quad Y \end{array}$$

| No. | $R_1$ | $R_2$ | $R_3$ | $R_4$ | Y | X | Absorption maximum wavelength in acetone (nm) |
|-----|-------|-------|-------|-------|---|---|----|
| 40 | H | H | CN | H | C=O | 4-[N-(n-$C_5H_{11}$)(N≡C-$C_2H_4$)amino]-2-(NHCOCH$_3$)phenyl | 724 |
| 41 | H | H | OCOOC$_2$H$_5$ | H | C=O | 4-[(C$_2$H$_5$)$_2$N]-2-CH$_3$-phenyl | 685 |
| 42 | H | H | H | CH$_3$ | C=O | 4-[(n-C$_5$H$_{11}$)$_2$N]-2-CH$_3$-phenyl | 695 |
| 43 | H | H | COOCH$_3$ | H | C=O | 4-[N-(n-C$_6$H$_{13}$)(C$_6$H$_5$O-(CH$_2$)$_4$-)amino]-2-(COCH$_3$)phenyl | 720 |
| 44 | H | H | H | CONHC$_4$H$_9$(n) | C=O | 4-[(C$_2$H$_5$)$_2$N]-2-CH$_3$-phenyl | 723 |
| 45 | H | H | OCH$_3$ | H | C=O | 4-[N-(n-C$_5$H$_{11}$)(N≡C-C$_2$H$_4$)amino]-2-(NHCOCH$_3$)phenyl | 698 |
| 46 | H | H | H | H | SO$_2$ | 4-[(C$_2$H$_5$)$_2$N]-2-(NHCOCH$_3$)phenyl | 675 |
| 47 | H | H | H | H | SO$_2$ | 4-[N-(n-C$_5$H$_{11}$)(N≡C-C$_2$H$_4$)amino]-2-(NHCOCH$_3$)phenyl | 650 |

TABLE 1-continued
General formula:
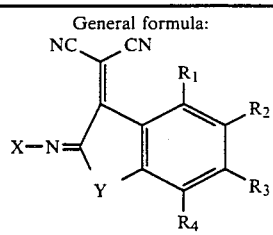
| No. | R₁ | R₂ | R₃ | R₄ | Y | X | Absorption maximum wavelength in acetone (nm) |
|---|---|---|---|---|---|---|---|
| 48 | H | H | H | H | SO₂ | 4-CH₃O, N(C₂H₅)(CH₃OCOC₂H₄)- phenyl | 641 |
| 49 | H | H | H | H | SO₂ | 4-CH₃COO, N(CH₃O(CH₂)₄)(n-C₅H₁₁)- phenyl | 672 |
| 50 | H | H | H | H | SO₂ | 4-NHSO₂CH₃, N(C₆H₁₃)₂- phenyl | 674 |
| 51 | H | H | H | H | SO₂ | 4-CH₃, N(C₂H₅)₂- phenyl | 712 |
| 52 | H | H | H | H | SO₂ | 4-CH₃, N(n-C₄H₉)₂- phenyl | 715 |
| 53 | H | H | H | H | SO₂ | 4-C₂H₅, N(C₂H₅)₂- phenyl | 712 |
| 54 | H | H | H | H | SO₂ | 3-CH₃O, 4-CH₃, N(C₂H₅)₂- phenyl | 725 |
| 55 | H | H | H | H | SO₂ | 3-CH₃O, 4-CH₃, N(HOC₂H₄)₂- phenyl | 724 |

TABLE 1-continued

General formula:

$$\begin{array}{c} NC \quad CN \\ \diagdown \quad \diagup \\ = \\ \diagup \quad \diagdown \\ X-N \quad \text{Ar}(R_1,R_2,R_3,R_4) \\ \parallel \\ Y \end{array}$$

| No. | R$_1$ | R$_2$ | R$_3$ | R$_4$ | Y | X | Absorption maximum wavelength in acetone (nm) |
|---|---|---|---|---|---|---|---|
| 56 | H | H | H | H | SO$_2$ | 9-ethylcarbazol-3-yl | 651 |
| 57 | H | H | H | H | SO$_2$ | 2-(diethylamino)-4-phenyl-5-methylthiazol-5-yl derivative | 702 |
| 58 | H | H | H | H | SO$_2$ | 1,1,4,4-tetramethyl-7-(dimethylamino)-1,2,3,4-tetrahydroquinolin-6-yl analog | 648 |
| 59 | H | H | H | H | SO$_2$ | 1,1,4,4-tetramethyl-7-(N-ethyl-methyl amino)-6,8-dimethyl analog | 718 |
| 60 | H | H | H | H | SO$_2$ | 1,1,4,4-tetramethyl-7-(N-n-butyl-methyl amino)-6,8-dimethyl analog | 717 |
| 61 | H | H | H | H | SO$_2$ | 1,1,4,4-tetramethyl-7-(N-2-hydroxyethyl-methyl amino)-6-ethyl-8-methyl analog | 719 |

TABLE 1-continued

General formula:

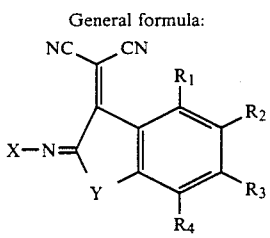

| No. | $R_1$ | $R_2$ | $R_3$ | $R_4$ | Y | X | Absorption maximum wavelength in acetone (nm) |
|---|---|---|---|---|---|---|---|
| 62 | H | H | H | H | $SO_2$ | (2-(N-ethyl-N-neopentyl)amino-5-methoxyphenyl)-2-methylethyl group | 660 |
| 63 | H | H | Cl | H | $SO_2$ | (2-(N-methyl-N-neopentyl)amino-5-methylphenyl)-2-methylethyl group | 680 |
| 64 | H | H | Br | H | $SO_2$ | 4-(N-n-pentyl-N-cyanoethyl)amino-2-benzoylamino-6-methylphenyl | 707 |
| 65 | H | H | $NO_2$ | H | $SO_2$ | (2-(N-ethyl-N-neopentyl)amino-5-methylphenyl)-2-methylethyl group | 730 |
| 66 | H | H | $NO_2$ | H | $SO_2$ | (2-(N-methyl-N-neopentyl)amino-5-methylphenyl)-2-methylethyl group | 729 |
| 67 | H | H | $NO_2$ | H | $SO_2$ | 8-(di-n-pentylamino)-5-methylquinolinyl | 715 |

TABLE 1-continued

General formula:

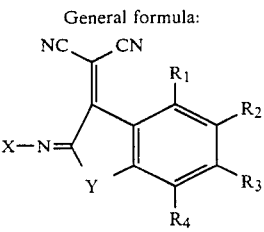

| No. | R₁ | R₂ | R₃ | R₄ | Y | X | Absorption maximum wavelength in acetone (nm) |
|---|---|---|---|---|---|---|---|
| 68 | H | H | NO₂ | H | SO₂ | 4-methyl-1-(N-methyl-N-neopentyl-like)... 2-(1-methylethyl) naphthalene derivative with N(CH₃)(CH₂C(CH₃)₃) and CH(CH₃) substituents | 730 |
| 69 | H | H | H | Cl | SO₂ | 4-(C₂H₅)₂N-2-methylphenyl | 725 |
| 70 | H | H | H | Cl | SO₂ | 4-(n-C₄H₉)₂N-2-methylphenyl | 726 |
| 71 | H | H | H | Cl | SO₂ | 4-[N-ethyl-N-neopentyl]amino-2,5-dimethylphenyl with CH(CH₃)CH₂C(CH₃)₃ group | 728 |
| 72 | H | H | H | Cl | SO₂ | 4-[N-n-butyl-N-neopentyl]amino-2,5-dimethylphenyl with CH(CH₃)CH₂C(CH₃)₃ group | 728 |
| 73 | H | H | OCH₃ | H | SO₂ | 4-(n-C₅H₁₁)₂N-2-methylphenyl | 682 |

TABLE 1-continued

General formula:

NC, CN, R1, R2, R3, R4, X-N=, Y

| No. | R1 | R2 | R3 | R4 | Y | X | Absorption maximum wavelength in acetone (nm) |
|---|---|---|---|---|---|---|---|
| 74 | H | H | NHCOCH$_3$ | H | SO$_2$ | 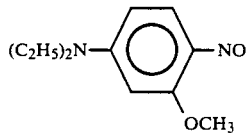 | 642 |

EXAMPLE 75

1.50 g of 1,3-disdicyanovinylindane and 2.50 g of the compound of the formula (7):

(C$_2$H$_5$)$_2$N—⌬—NO, OCH$_3$  (7)

were mixed in 40 ml of acetic anhydride and stirred at 20°~25° C. for 5 hours. The mixed solution was filtered, washed with ice-cold methanol and dried. The resulting product was recrystallized from chloroform to give 1.80 g of purified cakes of the compound of the following formula (8). Yield: 67.3%; melting point: above 300° C.

Absorbance in acetone: λmax=710 nm, ε=3.95×10$^4$.

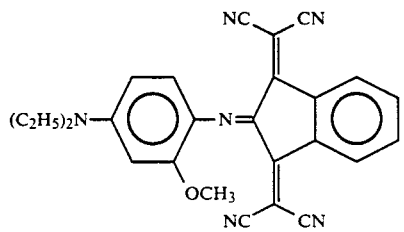

(8)

EXAMPLE 76

1.50 g of 1,3-bisdicyanovinylidane with 3.81 g of the compound of formula (9):

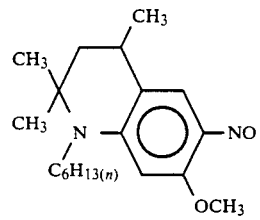

(9)

were mixed in 40 ml of acetic anhydride and stirred at 21°~25° C. for 8 hours. The mixed solution was filtered, washed with ice-cold methanol and dried. The resulting product was recrystallized from chloroform to give 2.06 g of purified cakes of the compound of the following formula (10). Yield: 53.2%; melting point: 247°~249° C. Absorbance in acetone solution: λmax=715 nm, ε=4.61×10$^4$.

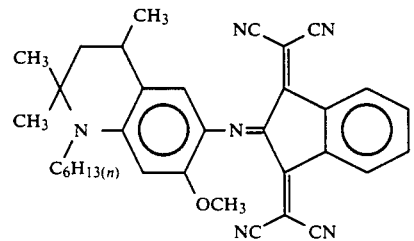

(10)

EXAMPLES 77-119

The compounds shown in Table 2 below were produced in the same way as Example 75 or Example 76.

TABLE 2

General formula:

X—N=[indene with =C(CN)₂ groups at 1,3-positions and benzene ring bearing R₁, R₂, R₃, R₄]

| No. | R₁ | R₂ | R₃ | R₄ | X | Absorption maximum wavelength in acetone (nm) |
|---|---|---|---|---|---|---|
| 77 | H | H | H | H | 4-[N(C₂H₄OH)₂]-2-(OC₂H₄OH)-phenyl | 711 |
| 78 | H | H | H | H | 4-[N(n-C₆H₁₃)₂]-2-(OCH₃)-phenyl | 709 |
| 79 | H | H | H | H | 4-[N(C₂H₄Br)₂]-2-(OCH₃)-phenyl | 712 |
| 80 | H | H | H | H | 4-[N(C₂H₅)(C₂H₄CN)]-2-(OCH₃)-phenyl | 711 |
| 81 | H | H | H | H | 4-(NH-C₆H₅)-2-(OH)-phenyl | 712 |
| 82 | H | H | H | H | 4-[N(CH₂C₆H₅)₂]-2-(OCH₃)-phenyl | 710 |
| 83 | H | H | H | H | 4-(morpholino)-2-(OCH₃)-phenyl | 708 |
| 84 | H | H | H | H | 4-[N(C₂H₅)(cyclohexyl)]-2-(OCH₃)-phenyl | 710 |

TABLE 2-continued

General formula:

$$X-N=\text{[indane-dicyanomethylene structure with } R_1, R_2, R_3, R_4 \text{]}$$

| No. | $R_1$ | $R_2$ | $R_3$ | $R_4$ | X | Absorption maximum wavelength in acetone (nm) |
|---|---|---|---|---|---|---|
| 85 | H | H | H | H | 4-N(C$_2$H$_5$)$_2$, 2-OC$_2$H$_5$ phenyl (methyl attached) | 710 |
| 86 | H | H | H | H | 4-N(C$_2$H$_5$)$_2$, 2-OC$_4$H$_{9(n)}$ phenyl | 711 |
| 87 | H | H | H | H | 4-N(CH$_3$)$_2$, 2-OCH$_2$-phenyl | 711 |
| 88 | H | H | H | H | 4-N(C$_2$H$_5$)$_2$, 2-Cl phenyl | 701 |
| 89 | H | H | H | H | 4-N(C$_2$H$_4$OC$_2$H$_5$)$_2$, 2-Cl phenyl | 703 |
| 90 | H | H | H | H | 4-N(C$_2$H$_4$COOCH$_3$)$_2$, 2-Br phenyl | 702 |
| 91 | H | H | H | H | 4-N(C$_2$H$_4$OCOCH$_3$)$_2$, 2-Br phenyl | 703 |
| 92 | H | H | H | H | 4-N(C$_2$H$_5$)(C$_2$H$_4$O-phenyl), 2-I phenyl | 704 |

TABLE 2-continued
General formula: 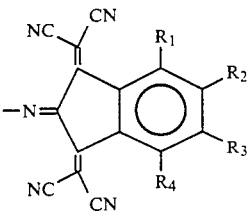
| No. | R₁ | R₂ | R₃ | R₄ | X | Absorption maximum wavelength in acetone (nm) |
|-----|----|----|----|----|----|------|
| 93 | H | H | H | H | 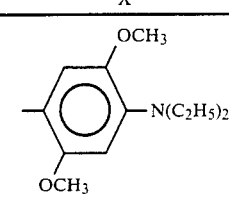 | 715 |
| 94 | H | H | H | H | 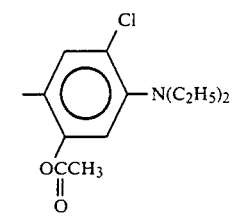 | 712 |
| 95 | H | H | H | H | 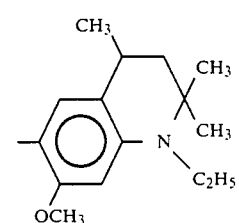 | 710 |
| 96 | H | H | H | H | 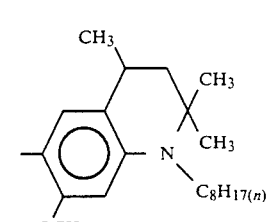 | 715 |
| 97 | H | H | H | H | 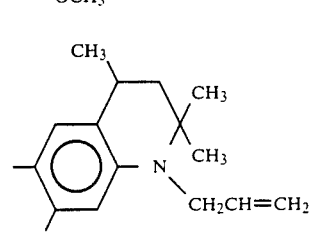 | 714 |
| 98 | H | H | H | H | | 713 |

TABLE 2-continued
General formula: 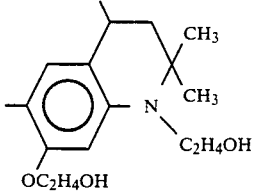
| No. | $R_1$ | $R_2$ | $R_3$ | $R_4$ | X | Absorption maximum wavelength in acetone (nm) |
|---|---|---|---|---|---|---|
| 99 | H | H | H | H | 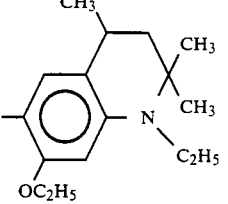 | 714 |
| 100 | H | H | H | H | 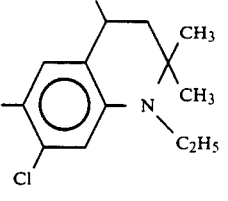 | 715 |
| 101 | H | H | H | H | 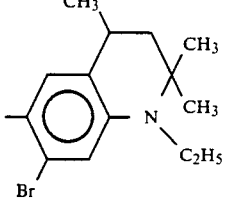 | 705 |
| 102 | H | H | H | H | 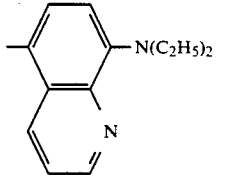 | 706 |
| 103 | H | H | H | H | 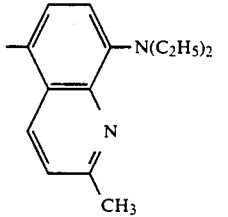 | 713 |
| 104 | H | H | H | H |  | 715 |

TABLE 2-continued
General formula:
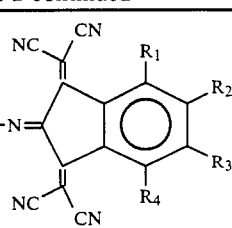
| No. | $R_1$ | $R_2$ | $R_3$ | $R_4$ | X | Absorption maximum wavelength in acetone (nm) |
|---|---|---|---|---|---|---|
| 105 | Cl | H | H | H | 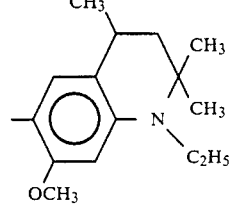 | 720 |
| 106 | Cl | H | H | H | 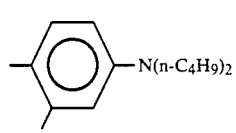 | 716 |
| 107 | Br | H | H | H | 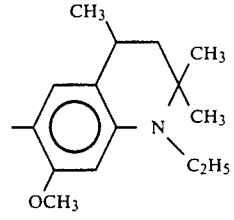 | 716 |
| 108 | I | H | H | H | 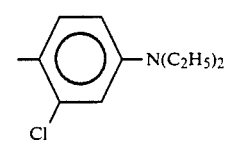 | 717 |
| 109 | $NO_2$ | H | H | H | 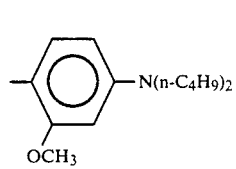 | 720 |
| 110 | H | CN | H | H | 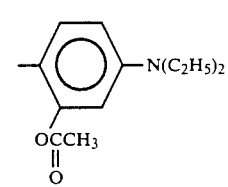 | 719 |
| 111 | $COOCH_3$ | H | H | H | | 720 |

TABLE 2-continued

General formula:

$$X-N=\text{[indandione-bis(dicyanomethylene) with R}_1, R_2, R_3, R_4\text{ on benzene ring]}$$

| No. | $R_1$ | $R_2$ | $R_3$ | $R_4$ | X | Absorption maximum wavelength in acetone (nm) |
|---|---|---|---|---|---|---|
| 112 | $CON(CH_3)_2$ | H | H | H | 4-methyl-2-(1,1-dimethylpropyl or 2-methylbutan-2-yl on ring)-5-methoxyphenyl with $N(CH_3)(C_2H_5)$ substituent (see structure) | 721 |
| 113 | H | OH | H | H | 4-methyl-3-ethoxyphenyl-$N(C_2H_5)_2$ | 705 |
| 114 | H | $OCH_3$ | H | H | 4-methyl-3-(n-butoxy)phenyl-$N(C_2H_5)_2$ | 700 |
| 115 | H | $OCOCH_3$ | H | H | 4-methyl-2-(2-methylbutan-2-yl)-5-methoxyphenyl-$N(CH_3)(n\text{-}C_4H_9)$ | 703 |
| 116 | H | $OCOO\text{-}C_6H_5$ | H | H | 4-methyl-3-methoxyphenyl-$N(n\text{-}C_4H_9)_2$ | 702 |
| 117 | $N(CH_3)_2$ | H | H | H | 4-methyl-3-ethoxyphenyl-$N(C_2H_4Br)_2$ | 691 |
| 118 | $CF_3$ | H | H | H | 4-methyl-2-(2-methylbutan-2-yl)-5-(2-hydroxyethoxy)phenyl-$N(CH_3)(C_2H_4OH)$ | 706 |

TABLE 2-continued

General formula:

$$X-N=\text{[indanylidene with NC/CN groups at positions, } R_1, R_2, R_3, R_4 \text{ on benzene ring]}$$

| No. | $R_1$ | $R_2$ | $R_3$ | $R_4$ | X | Absorption maximum wavelength in acetone (nm) |
|-----|-------|-------|-------|-------|---|---|
| 119 | $CH_3$ | H | H | H | –C₆H₃(OCH₃)–N(C₂H₅)₂ | 707 |

EXAMPLE 120

Figure 5:
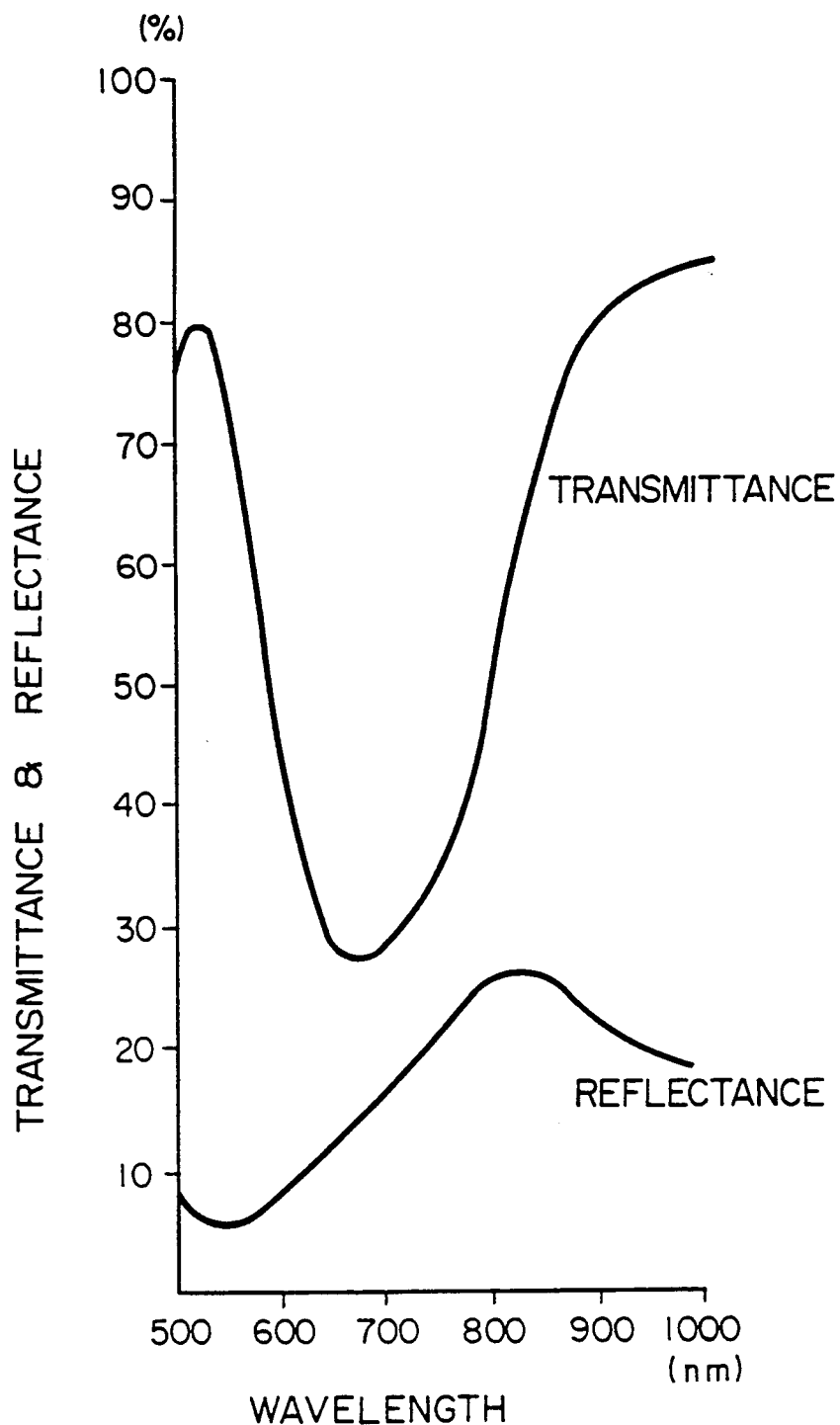
FIG. 5 shows the transmittance and reflectance spectra of the recording medium obtained in Example 120.

A trichloroethylene solution of the compound obtained in Example 1 was spin-coated onto a glass substrate at 4,000 r.p.m. for 20 seconds to form a 600 Å thick recording layer on said substrate to make an optical information recording medium. The transmittance and reflectance curves of the obtained recording medium are shown in FIG. 5.

When this recording medium was irradiated with a semiconductor laser of 780 nm is oscillation wavelength at 40 mJ/cm² with a spot diameter of 1 μm, the formation of a clear spot was observed.

EXAMPLE 121

Figure 6:
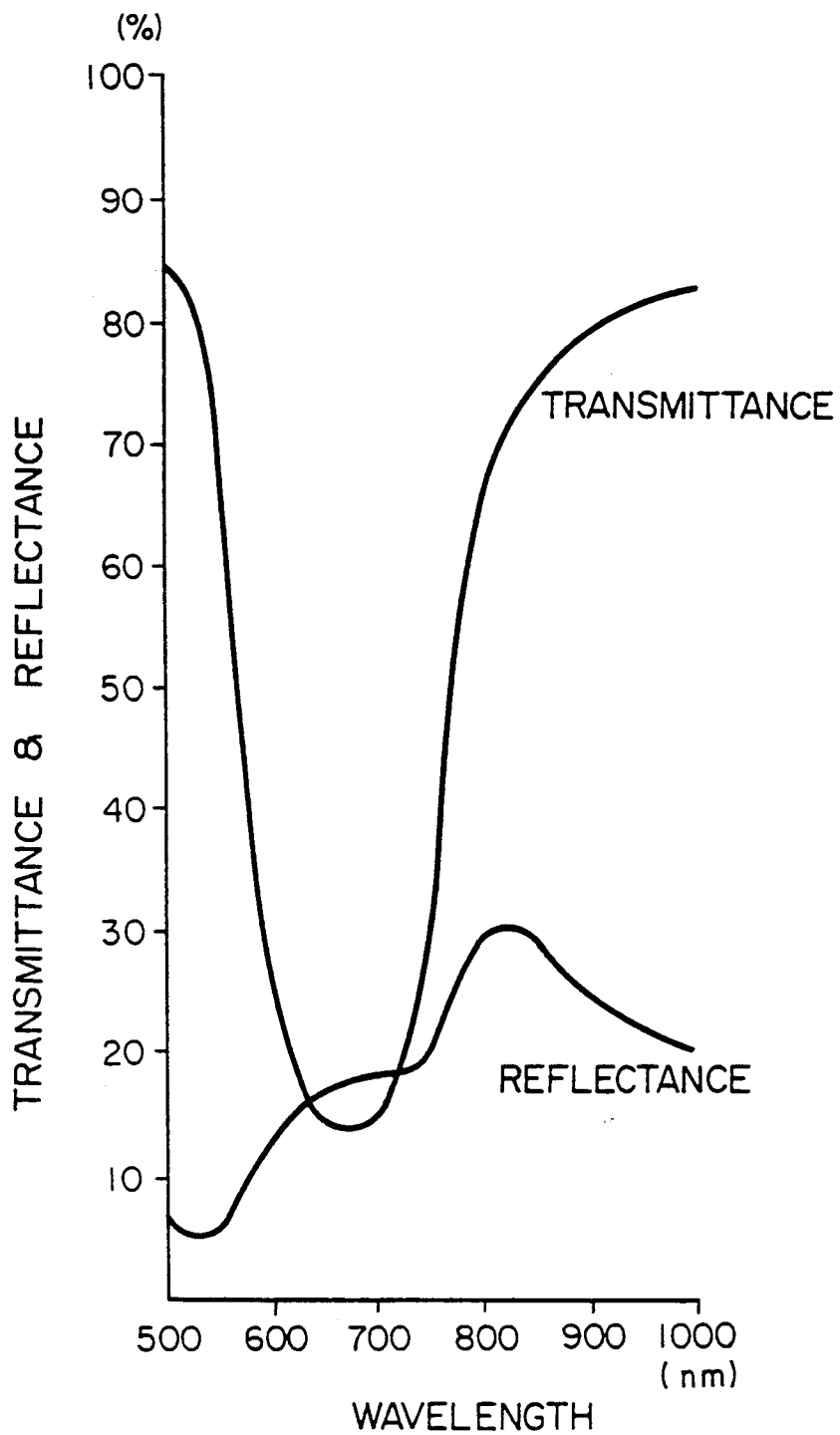
FIG. 6 shows the transmittance and reflectance spectra of the recording medium obtained in Example 121.

A chloroform solution of the compound obtained in Example 2 was spin-coated onto a glass substrate at 4,000 r.p.m. for 20 seconds to form a 600 Å thick recording layer on said substrate to make an optical information recording medium. The transmittance are reflectance curves of this recording medium are shown in FIG. 6.

When this recording medium was irradiated with a semiconductor laser of 780 nm is oscillation wavelength at 40 mJ/cm² with a spot diameter of 1 μm, the formation of a clear spot was observed.

EXAMPLE 122

Figure 7:
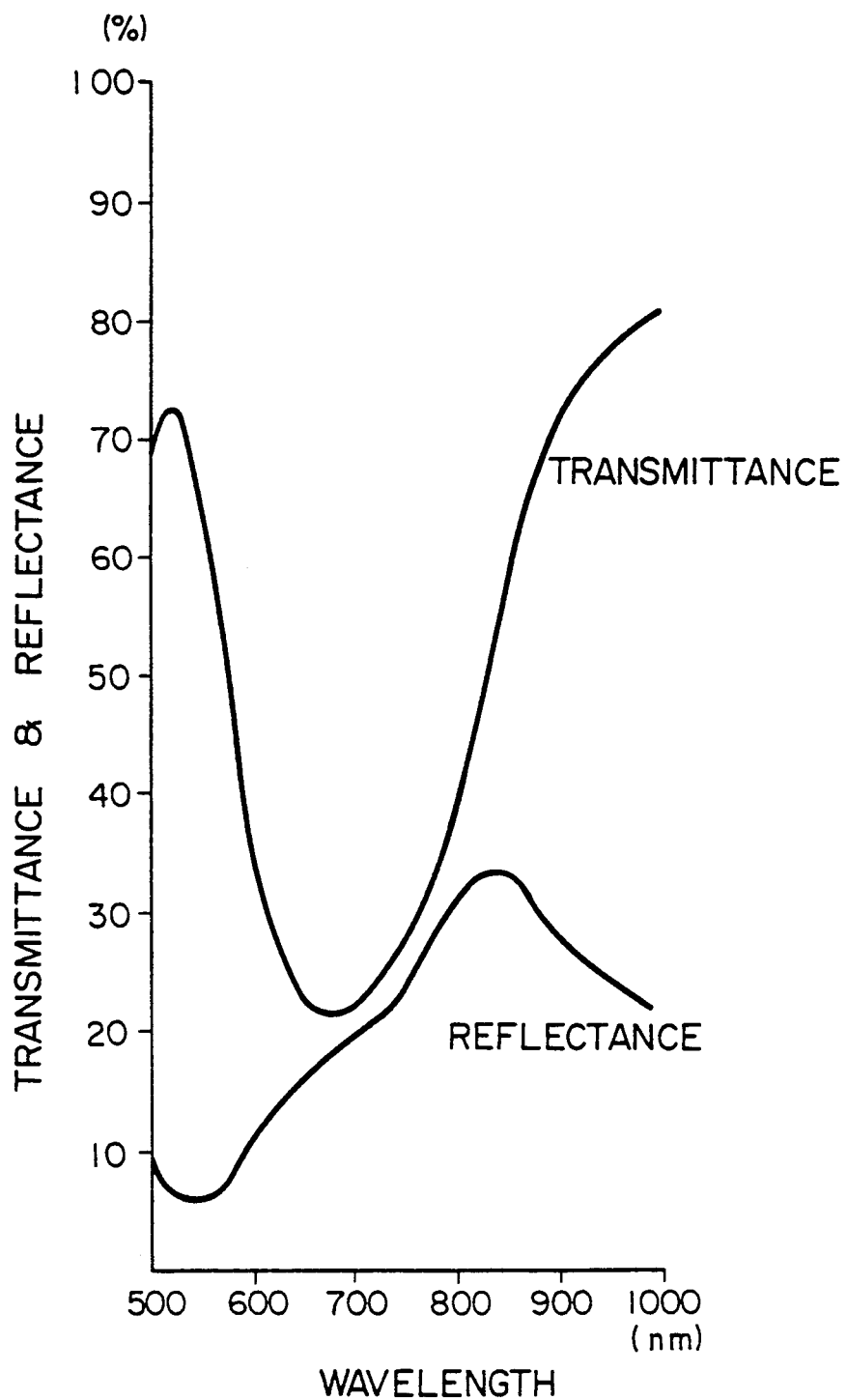
FIG. 7 shows the transmittance and reflectance spectra of the recording medium obtained in Example 122.

A chloroform solution of the compound obtained in Example 3 was spin-coated onto a glass substrate at 2,000 r.p.m. for 20 seconds to form a 800 Å thick recording layer on said substrate to make an optical information recording medium. The transmittance and reflectance curves of the obtained recording medium are shown in FIG. 7.

When this recording medium was irradiated with a semiconductor laser of 780 nm in oscillation wavelength at 40 mJ/cm² with a spot diameter of 1 μm, the formation of a clear spot was observed.

EXAMPLE 123

The dye used in Example 122 was vacuum deposited onto a PMMA substrate to form a 800 Å thick recording layer on said substrate to make a recording medium. Said vacuum deposition was carried out at a degree of vacuum below 3×10⁻⁵ Torr, a resistance heating boat temperature of 185°~195° C. and a deposition rate of about 0.5 Å/sec. The recording medium obtained showed similar transmittance and reflectance spectra to Example 122.

When this recording medium was irradiated with semiconductor laser of 780 nm is oscillation wavelength at 40 mJ/cm² with a spot diameter of 1 μm, the formation of a clear spot was observed.

EXAMPLE 124

Figure 8:
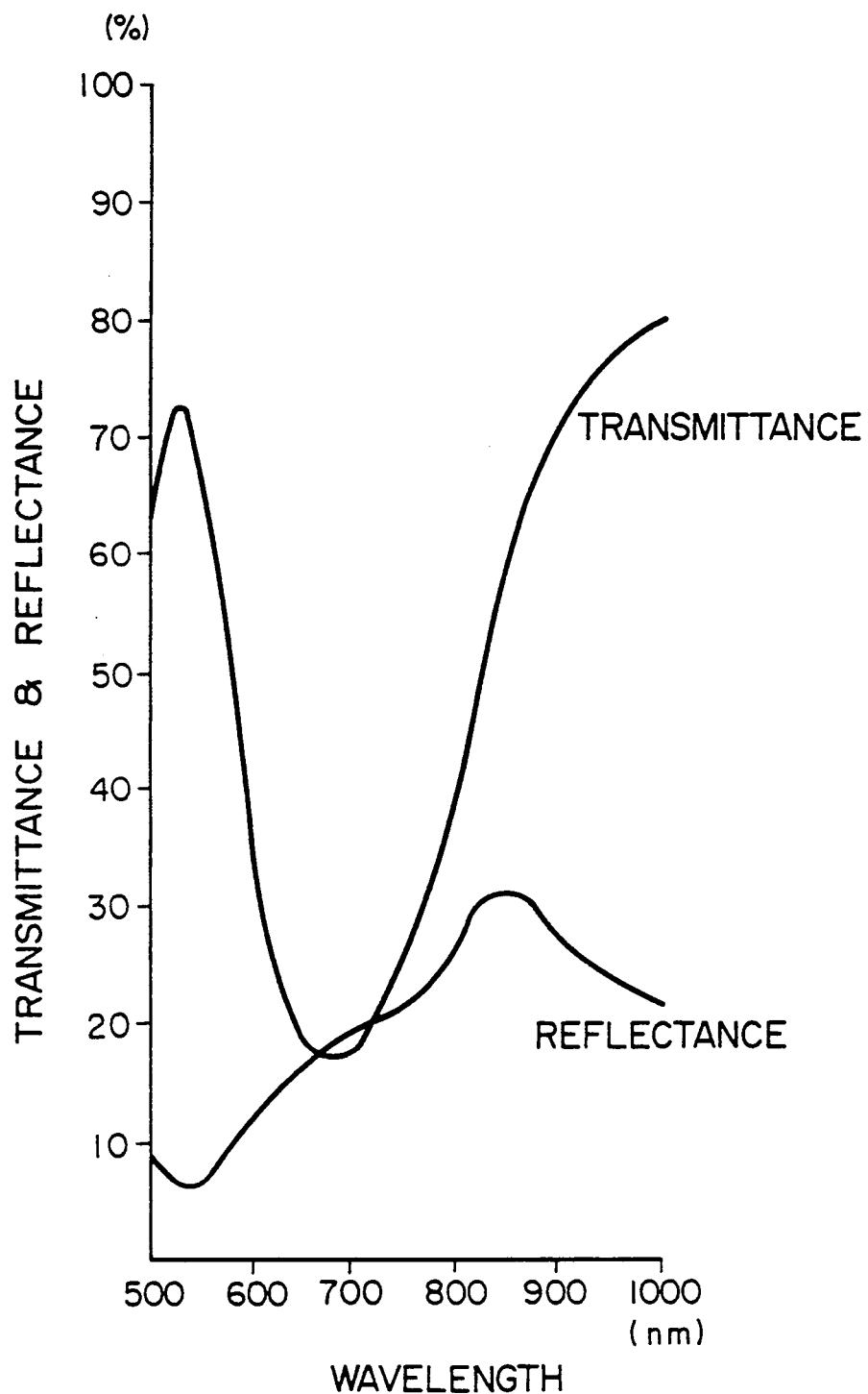
FIG. 8 shows the transmittance and reflectance spectra of the recording medium obtained in Example 124.

A tetrachloroethylene solution of the compound obtained in Example 17 was spin-coated onto a glass substrate at 2,000 r.p.m. for 20 seconds to form a 700 Å thick recording layer on said substrate to make an optical information recording medium. The transmittance and reflectance curves of the recording medium obtained are shown in FIG. 8.

When this recording medium was irradiated with a semiconductor laser of 780 nm in oscillation wavelength at 40 mJ/cm² with a spot diameter of 1 μm, the formation of a clear spot was observed.

EXAMPLE 125

The dye used in Example 124 was vacuum deposited onto a PMMA substrate to form a 700 Å thick recording layer on said substrate to make an optical information recording medium. Vacuum deposition was carried out at a degree of vacuum below 3×10⁻⁵ Torr, a resistance heating boat temperature of 195°~205° C. and a deposition rate of about 0.5 Å/sec. The recording medium obtained showed similar transmittance and reflectance spectra to Example 124.

When this recording medium was irradiated with a semiconductor laser of 780 nm in oscillation wavelength at 40 mJ/cm² with a spot diameter of 1 μm, the formation of a clear spot was observed.

EXAMPLE 126

Figure 9:
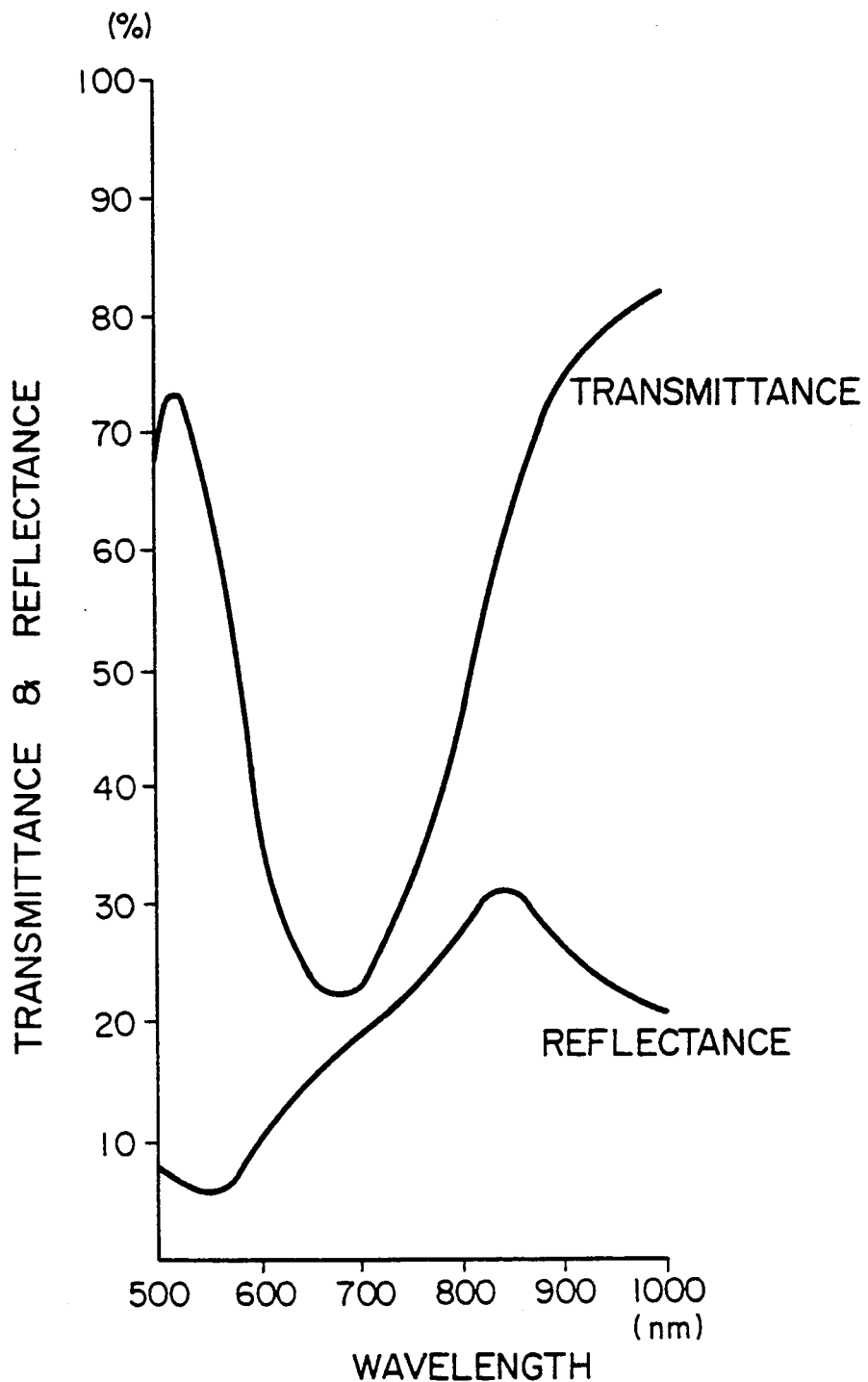
FIG. 9 shows the transmittance and reflectance curves of the recording medium obtained in Example 126.

A chloroform solution of the compound obtained in Example 31 was spin-coated onto a glass substrate at 2,000 r.p.m. for 20 seconds to form a 700 Å thick recording layer on said substrate to make an optical information recording medium. The transmittance and reflectance curves of the recording medium obtained are shown in FIG. 9.

When this recording medium was irradiated with a semiconductor laser of 780 nm is oscillation wavelength at 40 mJ/cm² with a spot diameter of 1 μm, the formation of a clear spot was observed.

EXAMPLE 127

The dye used in Example 126 was vacuum deposited onto a PMMA substrate to form a 700 Å thick recording layer on said substrate to make an optical information recording medium. Vacuum deposition was carried out at a degree of vacuum below $3 \times 10^{-5}$ Torr, a resistance heating boat temperature of 180°~190° C. and a deposition rate of about 0.5 Å/sec. The recording medium obtained showed similar transmittance and reflectance spectra to Example 124.

When this recording medium was irradiated with a semiconductor laser of 780 nm is oscillation wavelength at 40 mJ/cm² with a spot diameter of 1 μm, the formation of a clear spot was observed.

EXAMPLE 128

Figure 10:
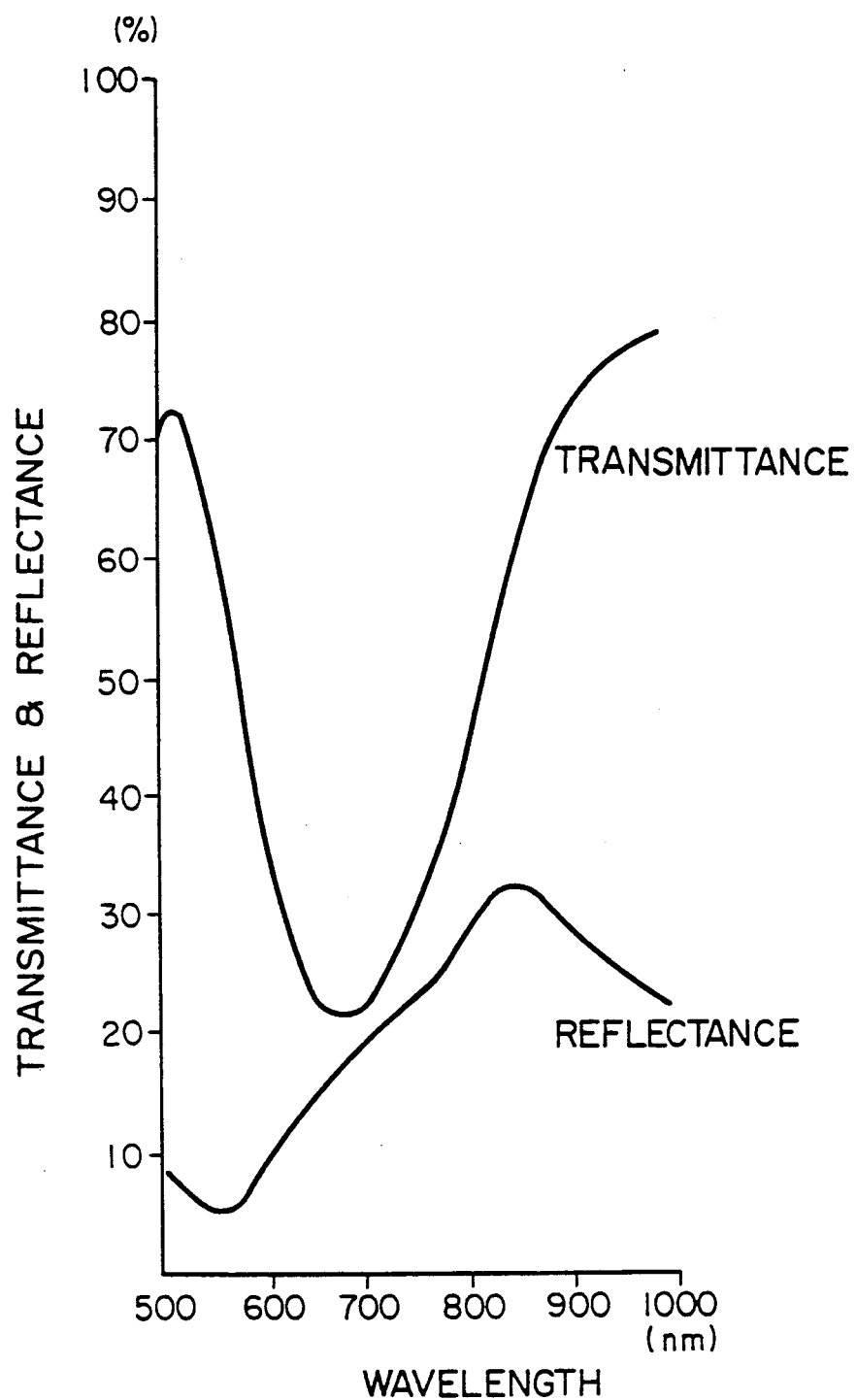
FIG. 10 shows the transmittance and reflectance curves of the recording medium obtained in Example 128.

A chloroform solution of 1:1 (by weight) mixture of the compound obtained in Example 17 and the compound obtained in Example 31 was spin-coated onto a glass substrate at 2,000 r.p.m. for 20 seconds to form a 700 Å thick recording layer on said substrate to make an optical information recording medium. The transmittance and reflectance curves of the recording medium obtained are shown in FIG. 10.

When this recording medium was irradiated with a semiconductor laser of 780 nm in oscillation wavelength at 40 mJ/cm² with a spot diameter of 1 μm, the formation of a clear spot was observed.

EXAMPLE 129

Figure 11:
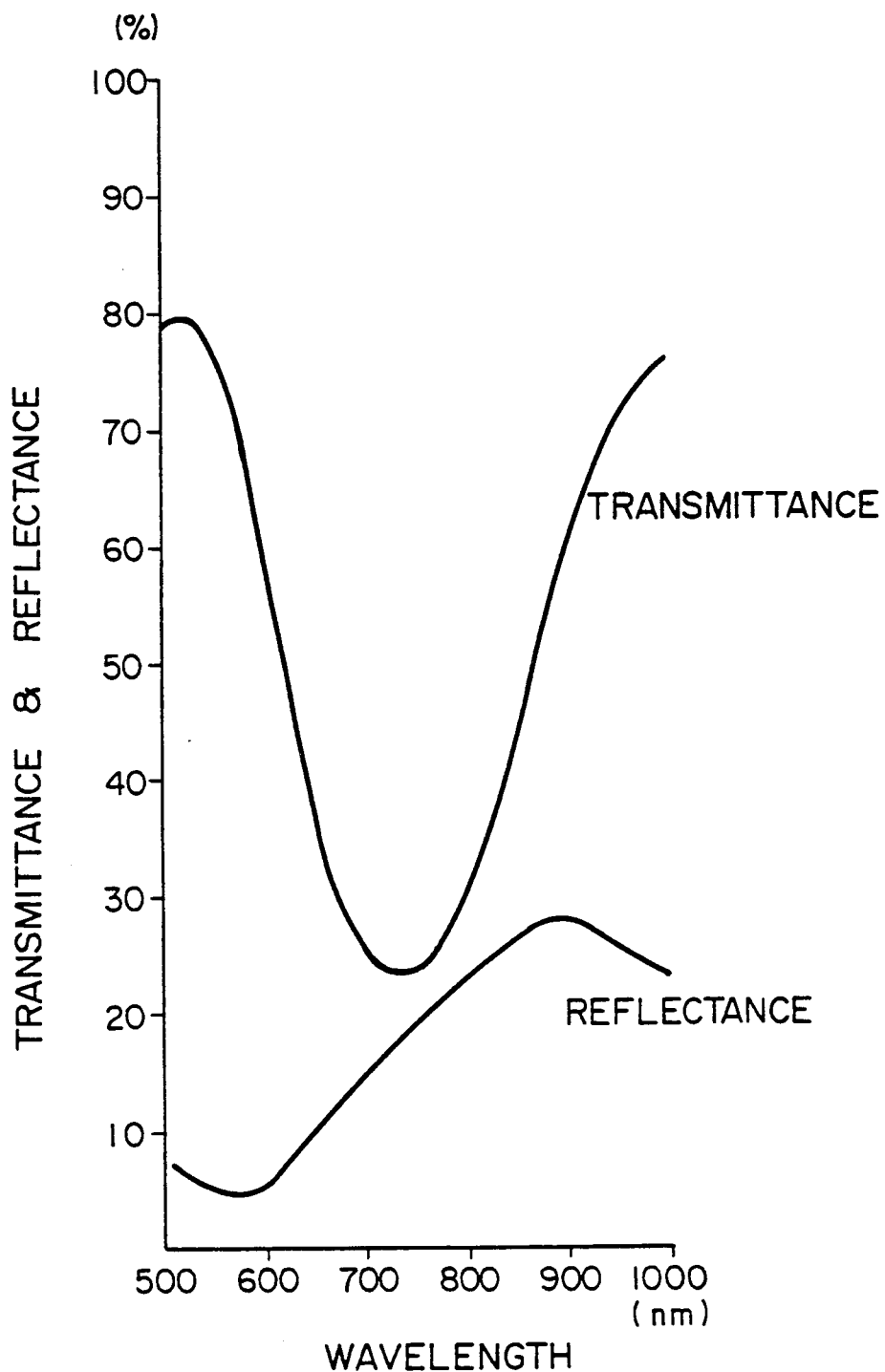
FIG. 11 shows the transmittance and reflectance curves of the recording medium obtained in Example 129.

A trichloroethylene solution of the compound obtained in Example 75 was spin-coated onto a glass substrate at 2,000 r.p.m. for 20 seconds to form an 800 Å thick recording layer on said substrate to make an optical information recording medium. The transmittance and reflectance curves of the recording medium obtained are shown in FIG. 11.

When this recording medium was irradiated with a semiconductor laser of 830 nm in oscillation wavelength at 40 mJ/cm² with a spot diameter of 1 μm, the formation of a clear spot was obtained.

EXAMPLE 130

Figure 12:
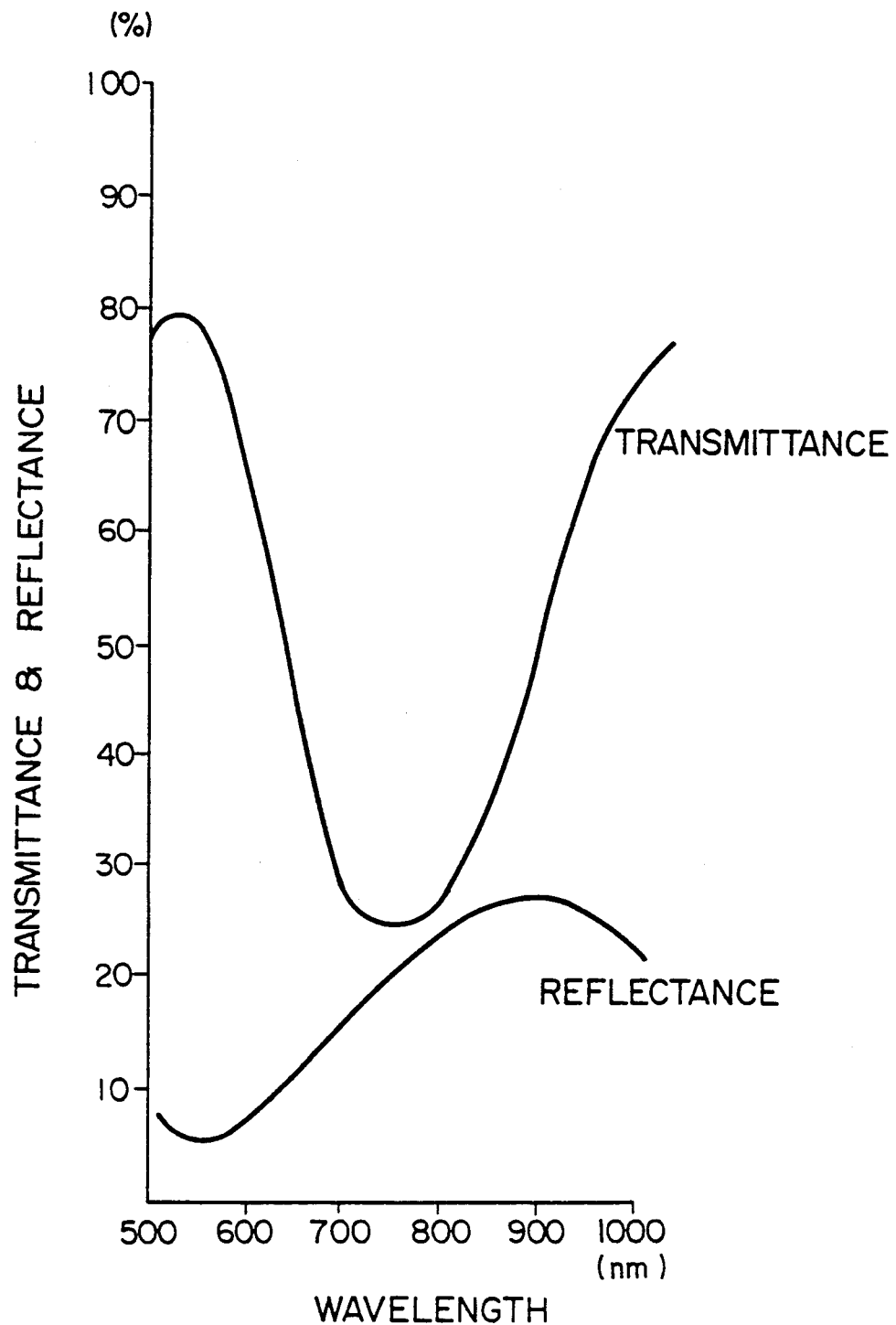
FIG. 12 shows the transmittance and reflectance curves of the recording medium obtained in Example 130.

A chloroform solution of the compound obtained in Example 76 was spin-coated onto a glass substrate at 2,000 r.p.m. for 20 seconds to form a 700 Å thick recording layer on said substrate to make an optical information recording medium. The transmittance and reflectance curves of the recording medium obtained are shown in FIG. 12.

When this recording medium was irradiated with a semiconductor laser of 830 nm in oscillation wavelength at 40 mJ/cm² with a spot diameter of 1 μm, the formation of a clear spot was obtained.

Comparative Example 1

Figure 13:
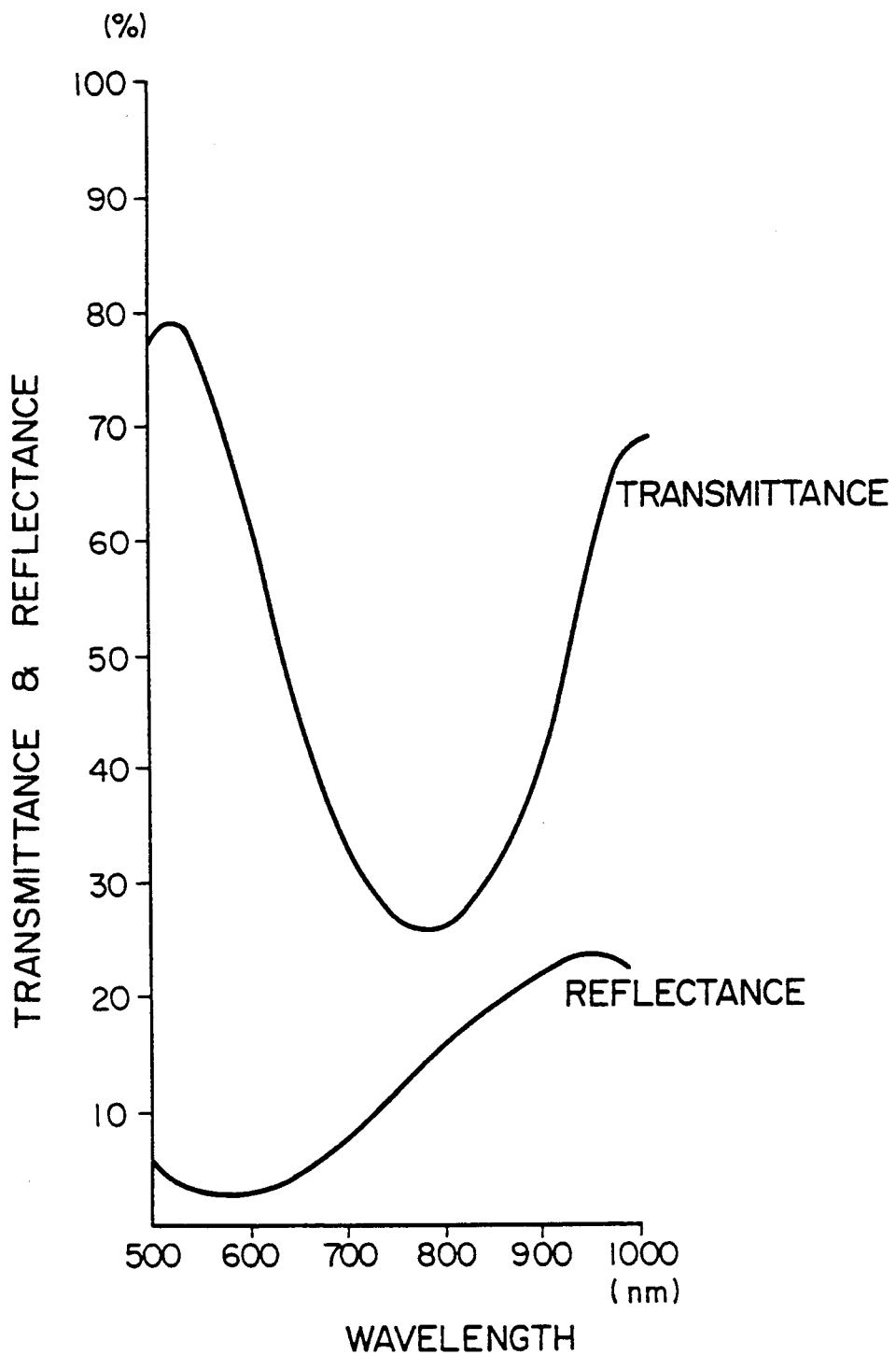
FIG. 13 shows the transmittance and reflectance curves of the recording medium obtained in Comparative Example 1.

A chloroform solution of the compound of the following structural formula was spin-coated onto a glass substrate at 2,000 r.p.m. for 20 seconds to form a 700 Å thick recording layer on said substrate to make an optical information recording medium. The transmittance and reflectance curves of the recording medium obtained are shown in FIG. 13. As seen from FIG. 13, this recording medium does not show high reflectance in the oscillation wavelength region of the semiconductor laser.

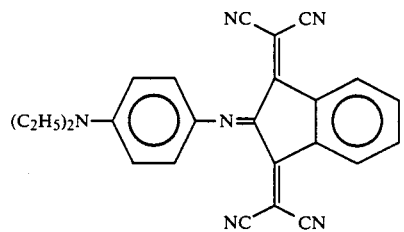

What is claimed is:

1. Azamethine compounds represented by formula (I)

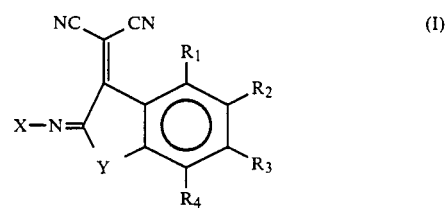

wherein
X represents

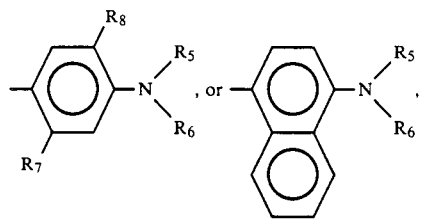

Y represents C=O;
$R_1$–$C_4$ represent individually hydrogen, halogen, nitro, cyano, hydroxy, —COOR, —OCOOR, —CONRR′, alkyl which is unsubstituted or substituted by halogen, alkoxy or amino which is substituted by alkyl; R and R′ represent independently hydrogen, alkyl or phenyl;

$R_5$ and $R_6$ represent independently hydrogen, phenyl, cyclohexyl, or alkyl which is unsubstituted or substituted by alkoxy, phenyl or

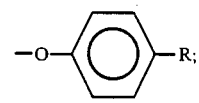

$R_7$ and $R_8$ represent independently hydrogen, alkoxy, hydroxy, halogen, —COR, —NHCOR or alkyl which is unsubstituted or substituted by phenyl; and R is as previously defined.

2. The azamethine compounds according to claim 1, wherein
X represents

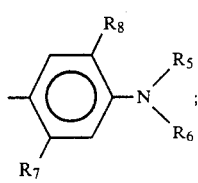

R₇ represents hydrogen, halogen, alkyl which is unsubstituted or substituted by phenyl; and R₈ represents hydrogen, halogen, alkyl or alkoxy.

3. The azamethine compounds according to claim 2, wherein R₇ represents alkyl which is unsubstituted or substituted by phenyl.

4. The azamethine compounds according to claim 2, wherein R₇ represents alkoxy.

5. Azamethine compounds represented by formula (I):

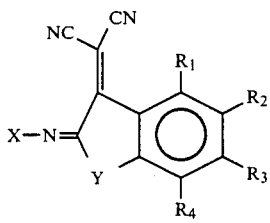

wherein
X represents

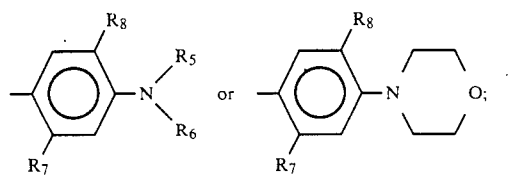

Y represents $C=C(CN)_2$;

$R_1$–$R_4$ represent independently hydrogen, halogen, nitro, cyano, hydroxy, —COOR, —OCOOR, —CONRR′, alkyl which is unsubstituted or substituted by halogen, alkoxy or amino which is substituted by alkyl; R and R′ represent independently hydrogen, alkyl or phenyl;

$R_5$ and $R_6$ represent independently hydrogen, phenyl, cyclohexyl or alkyl which is unsubstituted or substituted by halogen, alkoxy, phenyl or

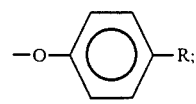

R is as defined above;

R₇ represents hydroxy, alkoxy which is unsubstituted or substituted by hydroxy or phenyl, halogen or —COOR″; R″ represents alkyl; and R₈ represents hydrogen, halogen, alkyl or alkoxy.

6. The azamethine compounds according to claim 5, wherein R₇ represents alkoxy which is unsubstituted or substituted by hydroxy or phenyl.

* * * * *